(12) United States Patent
Tagami et al.

(10) Patent No.: US 6,313,303 B1
(45) Date of Patent: Nov. 6, 2001

(54) PROCESS FOR THE PREPARATION OF PYRIDINE DERIVATIVES

(75) Inventors: Katsuya Tagami, Ibaraki; Nobuo Niikawa, Chiba; Akio Kayano; Hirofumi Kuroda, both of Ibaraki, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/462,180

(22) PCT Filed: Jul. 10, 1998

(86) PCT No.: PCT/JP98/03113

§ 371 Date: Jan. 3, 2000

§ 102(e) Date: Jan. 3, 2000

(87) PCT Pub. No.: WO99/02521

PCT Pub. Date: Jan. 21, 1999

(30) Foreign Application Priority Data

Jul. 11, 1997 (JP) .................................................. 9-186095
Jul. 23, 1997 (JP) .................................................. 9-197119
Apr. 28, 1998 (JP) ................................................ 10-117706

(51) Int. Cl.[7] .............................................. C07D 401/00
(52) U.S. Cl. .................................................... 546/273.4
(58) Field of Search .......................................... 546/273.4

(56) References Cited

U.S. PATENT DOCUMENTS 4,045,563 * 8/1977 Berntsson et al. .
5,374,730 12/1994 Slemon et al. ........................ 546/271

FOREIGN PATENT DOCUMENTS 05-93463 * 11/1997 (EP) .
52-62275 5/1977 (JP) .
56-142286 11/1981 (JP) .
61-205211 9/1986 (JP) .
1-484265 5/1992 (JP) .
3-52887 7/1993 (JP) .
5-507714 * 11/1993 (JP) .

OTHER PUBLICATIONS

M. Fieser, Fieser and Fieser's Reagents for Organic Synthesis, U.S. New York, vol. 12 12, 1986, p. 452 (XP–002109649).
Paquette L A, Encyclopedia of Reagents for Organic Synthesis, vol. 7, 1995, pp. 4611–4613 (XP002109650).

* cited by examiner

Primary Examiner—Alan L. Rotman
Assistant Examiner—Binta Robinson
(74) Attorney, Agent, or Firm—Birch, Stewart, Kolasch & Birch, LLP

(57) ABSTRACT

Processes for preparing sulfoxides useful as drugs such as acid secretion inhibitors or antiulcer drugs or intermediates for the preparation of drugs in high yields, at high purities, and with safety. Specifically, a process for the preparation of sulfoxides (II) by oxidizing a thio ether (I) with a peroxoborate salt in the presence of an acid anhydride or a metal catalyst; and a process for the preparation of sulfoxides (II) by oxidizing a thio ether (I) with an N-halosuccinimide, 1,3-dihalo-5,5-dimethyl-hydantoin or dichloroisocyanuric acid salt in the presence of a base. In said formulae $R^1$ is hydrogen, methoxy or difluoromethoxy; $R^2$ is methyl or methoxy; $R^3$ is 3-methoxypropoxy, methoxy or 2,2,2-trifluoroethoxy; and $R^4$ is hydrogen or methyl

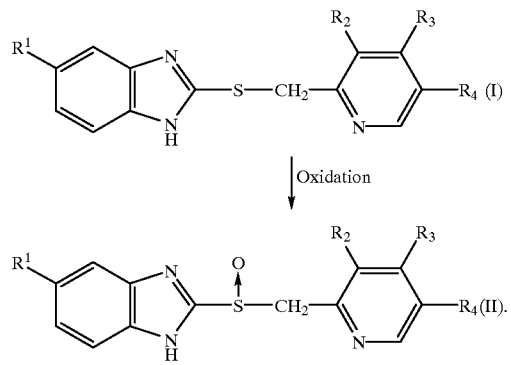

35 Claims, 1 Drawing Sheet

PROCESS FOR THE PREPARATION OF PYRIDINE DERIVATIVES

This application is the national phase under 35 U.S.C. §371 of PCT International Application No. PCT/JP98/03113 which has an International filing date of Jul. 10, 1998, which designated the United States of America.

FIELD OF THE INVENTION

The present invention relates to a method for producing a sulfoxide which is useful as a medicament such as an inhibitor of gastric acid secretion or an anti-ulcer agent or an intermediate for producing medicaments, as described in JP-A 1-6270 (Example 32), JP-A61-50978 (Example 2), JP-A54-141783 (Example 21), JP-A61-22079 etc., in a good yield at a high purity with safety.

PRIOR ART

Conventionally, sulfoxide has been produced by oxidizing thioether with oxidants such as hydrogen peroxide, m-chloroperbenzoic acid, sodiumhypochlorite, and sodiumbromite, as described in JP-A 1-6270 (EP-268956, U.S. Pat. No. 5,045,552), JP-A 61-50978 (EP-174726, U.S. Pat. No. 4,628,098), JP-A 54-141783 (EP-5129, U.S. Pat. No. 4,255,431) or JP-A 61-22079 (EP-166287, U.S. Pat. No. 4,758,579). (See the following formula, wherein $R^1$ to $R^4$ have the same meanings as described below).

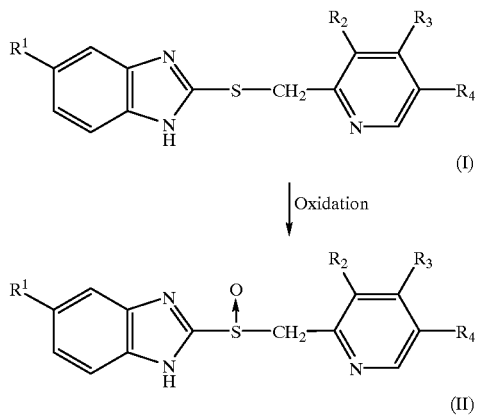

Among the above oxidants, from viewpoints of readiness in weighing, storage stability and reaction activity and the like, m-chloroperbenzoic acid is frequently used.

In Example 32 of JP-A 1-6270, for example, thioether is oxidized by using 0.96 equivalent (on a purity basis) of m-chloroperbenzoic acid, to produce sulfoxide at a yield of 80%, which is not an industrially satisfactory yield.

Depending on the reaction conditions, disadvantageously, the reaction does not ceased at the stage of sulfoxide production but further proceeds to a side reaction where a part of the produced sulfoxide is furthermore oxidized to sulfone as shown in the following reaction scheme. When sulfone is formed, there is a problem not only that the yield of the objective sulfoxide is reduced, but also that it is difficult to separate and purify them, since there is a close resemblance in physicochemical property between the two. (In the formula, $R^1$ to $R^4$ have the same meanings as described below.)

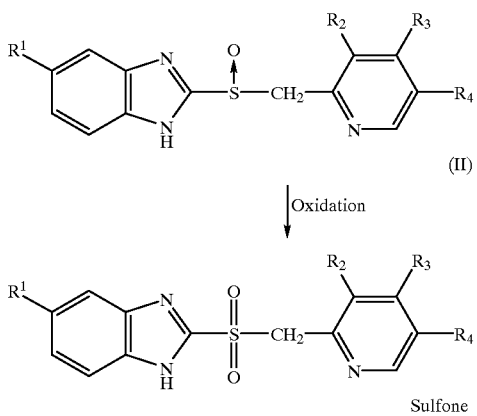

In JP-A 1-6270 and the like, additionally, the oxidation is conducted in dichloromethane (methylene chloride), but from a viewpoint of environmental strategies, there is a problem that halogenated hydrocarbon solvents can never be used industrially.

Additionally, since m-chloroperbenzoic acid is expensive, it is extremely disadvantageous from a viewpoint of the production cost. Still additionally, m-chloroperbenzoic acid is listed as a dangerous material and therefore requires deep attention for the use and storage thereof, inconveniently for large-scale handling.

As has been described above, no industrially excellent method for producing sulfoxide (II) has been established yet. Accordingly, a novel excellent method for producing sulfoxide (II) has been required.

DISCLOSURE OF THE INVENTION

The present inventors have made intensive investigations so as to solve the above-mentioned problems. As a result, they have found that the objective sulfoxide (II) can be produced in a good yield with no formation of a byproduct sulfone, safety, with no use of any halogenated hydrocarbon solvent. Thus, they have accomplished the present invention.

The present invention is a method for producing sulfoxide (II) represented by the following formula (II):

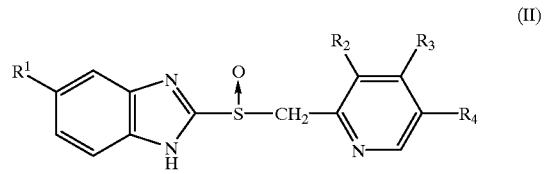

(wherein $R^1$ to $R^4$ have the same meanings as described below), which comprises the step of oxidizing thioether (I) represented by the following formula (I):

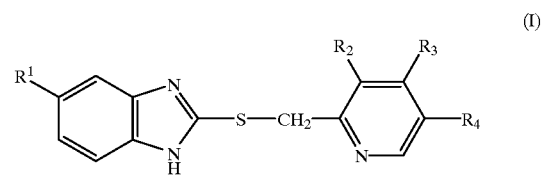

(wherein $R^1$ represents hydrogen atom, methoxy group or difluoromethoxy group; $R^2$ represents methyl group or methoxy group; $R^3$ represents 3-methoxypropoxy group, methoxy group or 2,2,2-trifluoroethoxy group; and $R^4$ represents hydrogen atom or methyl group) with a). a perborate in the presence of an acid anhydride or a metal catalyst, or b). N-halosuccinimide, 1,3-dihalo-5,5-dimethylhydantoin or dichloroisocyanurate in the presence of a base.

More specifically, thioether (I) is a compound which is identical to 2-{[4-(3-methoxypropoxy)-3-methylpyridin-2-yl]methylthio}-1H-benzimidazole described in JP-A 1-6270 (Example 31), the compound described in JP-A 61-50978 (Example 1) ($R^1$=H, $R^2$=CH$_3$, $R^3$=H, $R^4$=CH$_2$CF$_3$ and n=0; chemical name: 2-{[4-(2,2,2-trifluoroethoxy)-3-methylpyridin-2-yl]methylthio}-1H-benzimidazole), 5-methoxy-2-[(4-methoxy-3,5-dimethyl-2-pyridyl) methylthio]-1H-benzimidazole as a precursor of the compound described in JP-A 54-141783 (Example 21) or 5-difluoromethoxy-2-[(4,5-dimethoxy-2-pyridyl) methylthio]-1H-benzimidazole as a precursor of the compound described in JP-A 61-22079, and is a starting material of the present invention. All the compounds can be produced by the methods described in each publication.

More specifically, sulfoxide (II) is identical to 2-{[4-(3-methoxypropoxy)-3-methylpyridin-2-yl]methylsulfinyl}-1H-benzimidazole (general name: Rabeprazole free base) described in JP-A 1-6270 (Example 32), the compound described in JP-A 61-50978 (Example 2) ($R^1$=H, $R^2$=CH$_3$, $R^3$=H, $R^4$=CH$_2$CF$_3$ and n=1; general name: Lansoprazole; chemical name: 2-{[4-(2,2,2-trifluoroethoxy)-3-methylpyridin-2-yl]methylsulfinyl}-1H-benzimidazole), 5-methoxy-2-[(4-methoxy-3,5-dimethyl-2-pyridyl) methylsulfinyl]-1H-benzimidazole (general name: Omeprazole) described in JP-A 54-141783 (Example 21) or 5-difluoromethoxy-2-[(4,5-dimethoxy-2-pyridyl) methylsulfinyl]-1H-benzimidazole (general name: Pantoprazole) described in JP-A 61-22079, and is the objective compound of the present invention.

More specifically, sulfoxide (II) includes for example the following compounds:

Omeprazole

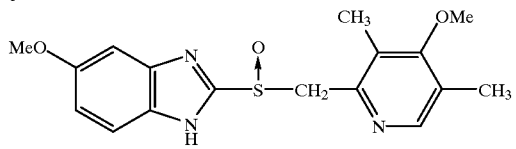

Lansoprazole

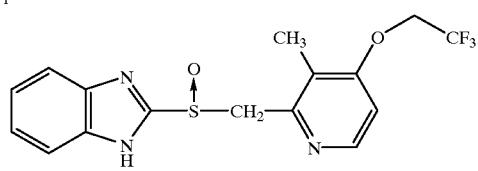

Rabeprazole (free base)

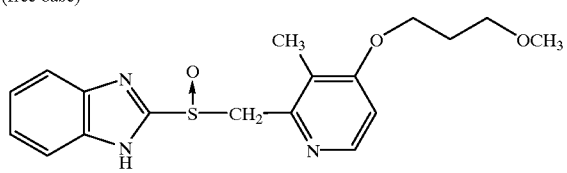

Pantoprazole

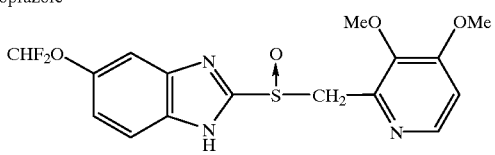

The method of production of the present invention is now described in detail.

The present invention encompasses the embodiments a) and b) described above.

The embodiments a) and b) are described hereinafter.

The type of perborate which is an oxidant used in the embodiment a) is not limited, but generally, the sodium perborate is preferable. Further, the perborate may occasionally form a hydrate at no limited hydration quantity, and generally, tetrahydrate or monohydrate is preferable. Additionally, sodium perborate·tetrahydrate (NaBO$_3$.4H$_2$O; CAS Registration No. 10486-00-7) and sodium perborate·monohydrate (NaBO$_3$.H$_2$O; CAS Registration No. 10332-33-9) are commercially available as reagents and industrial raw materials and the like.

The amount of perborate to be used is not also limited, but generally it is used in the range of from 0.8 to 1.7 equivalents, more preferably from 0.85 to 1.6 equivalents and further preferably from 0.9 to 1.5 equivalents to thioether (I).

The type of N-halosuccinimide which is an oxidant used in the embodiment b) is not also limited, but generally, N-chlorosuccinimide (CAS Registration No. 128-09-6) or N-bromosuccinimide (CAS Registration No. 128-08-5) is preferable. Additionally, N-halosuccinimide is also commercially available as a reagent and an industrial raw material and the like.

The amount of N-halosuccinimide to be used is not also limited, but generally it is used in the range of from 0.8 to 1.7 equivalents, more preferably from 0.85 to 1.6 equivalents and further preferably from 0.9 to 1.5 equivalents to thioether (I).

Next, the type of 1,3-dihalo-5,5-dimethylhydantoin used in the embodiment b) is not also limited, but generally, 1,3-dichloro-5,5-dimethylhydantoin (CAS Registration No. 118-52-5) or 1,3-dibromo-5,5-dimethylhydantoin (CAS Registration No. 77-48-5) is preferable. Additionally, 1,3-dihalo-5,5-dimethylhydantoin is also commercially available as a reagent and an industrial raw material and the like.

The amount of 1,3-dihalo-5,5-dimethylhydantoin is not also limited, but generally it is used in the range of from 0.3 to 1.0 equivalent, more preferably from 0.35 to 0.9 equivalent, further preferably from 0.4 to 0.8 equivalent to thioether (I).

The type of dichloroisocyanurate used in the embodiment b) is not also limited, but generally, sodium dichloroisocyanurate (CAS Registration No. 2893-78-9) or potassium dichloroisocyanurate (CAS Registration No. 2244-21-5) is preferable. Furthermore, the dichloroisocyanurate is also commercially available as reagents and industrial raw materials and the like.

The amount of dichloroisocyanurate to be used is not limited, but generally it is used in the range of from 0.3 to 1.0 equivalent, more preferably from 0.35 to 0.9 equivalent, further preferably from 0.4 to 0.8 equivalent to thioether (I).

Next, the reaction is conducted in the presence of an acid anhydride or a metal catalyst in the embodiment a). The presence of any one of the two is satisfactory.

The acid anhydride in the embodiment a) is not limited so long as it is prepared by dehydrating together carboxylic acids which may be the same or different, or by subjecting a bifunctional carboxylic acid to dehydration within the molecule. More specifically, it includes for example acetic anhydride, propionic anhydride, butyric anhydride, succinic anhydride, maleic anhydride, benzoic anhydride or phthalic anhydride or the like. Generally, using acetic anhydride and propionic anhydride brings about more excellent results.

The amount of the acid anhydride used is not also limited, but generally it is used in the range of from 0.8 to 1.7 equivalents, more preferably from 0.85 to 1.6 equivalents, further preferably from 0.9 to 1.5 equivalents to thioether (I).

Additionally, the most preferable result can be observed when the amount of acid anhydride used is in the range of from 1.0 to 2.0 equivalents to a perborate and from 0.9 to 1.5 equivalents to thioether (I).

The metal catalyst in the embodiment a) specifically includes vanadium pentaoxide ($V_2O_5$), vanadyl acetylacetonate (($CH_3COCHCOCH_3)_2VO$), molybdenum oxide acytlacetonate (($CH_3COCHCOCH_3)_2MoO_2$), ammonium heptamolybdate tetrahydrate (($NH_4)_6$ $Mo_7O_{24}.4H_2O$), ammonium molybdate (($NH_4)_2MoO_4$), sodium vanadate ($NaVO_3$), titanium tetraisopropoxide (Ti $[OCH(CH_3)_2]_4$), titanium trichloride ($TiCl_3$), tellurium dioxide ($TeO_2$), selenium dioxide ($SeO_2$), methyl trioxorhenium ($CH_3ReO_3$) or tungsten oxide ($WO_3$), and vanadyl acetylacetonate is the most preferable.

The amount of the metal catalyst to be used is not limited, but the use in an amount of 0.05 to 0.15 equivalent to a perborate brings about a preferable result.

Next, in the embodiment b), reaction is conducted in the presence of a base. Herein, the base used in the embodiment b) is not limited so long as it is inert to thioether (I), sulfoxide (II) or oxidants, but generally, inorganic bases are preferable. More specifically, the base includes for example sodium hydroxide, potassium hydroxide, lithium hydroxide, sodium carbonate, potassium carbonate, sodium hydrogencarbonate, potassium hydrogencarbonate, sodium phosphate, potassium phosphate, sodium hydrogenphosphate, sodium formate, potassium formate, sodium acetate, potassium acetate and the like, and additionally includes mixtures of two or more thereof.

The amount of base to be used is not limited, but generally, it ranges from 0.8 to 4.0 equivalents, more preferably 0.85 to 3.5 equivalents and further preferably 0.9 to 3.0 equivalents to N-halosuccinimide.

Additionally, the base is generally used in an amount of 0.4 to 2.0 equivalents, more preferably 0.4 to 1.75 equivalents and further preferably 0.4 to 1.5 equivalents to 1,3-dihalo-5,5-dimethylhydrantoin or dichloroisocyanurate.

For the reaction, any solvent inactive to thioether I, sulfoxide II, further the perborate salt in the embodiment a) or the oxidant or base in the embodiment b) may be used singly or in combination, with no limitation. Generally in the embodiment a), methanol, ethanol, propanol, mixture solvents such as methanol/toluene, ethanol/toluene, propanol/toluene, water/methanol, water/ethanol, water/propanol and toluene/dimethylformamide, or acetic acid brings about a preferable results. Preferable results are brought about in the embodiment b), by using one or more of N,N-dimethylformamide, acetonitrile, toluene, tetrahydrofuran, lower fatty acid esters and water. The solvent may be a mixture.

As the solvent in the embodiment b), a combination of one or more solvents selected from N,N-dimethylformamide, acetonitrile, toluene, tetrahydrofuran and lower fatty acid esters in the presence of water is further preferable, and it brings about more excellent results.

The amount of water to be used is not limited, but generally, it ranges in amount from 0.1 to 50 ml, more preferably 0.25 to 20 ml and further preferably 0.5 to 10 ml per 1 g of thioether (I).

The lower fatty acid esters in the embodiment b) are not limited so long as they are formed by dehydrating together a lower fatty acid having 6 or less carbon atoms and a lower alcohol having 6 or less carbon atoms. The concrete examples thereof include methyl formate, ethyl formate, propyl formate, butyl formate, amyl formate, methyl acetate, ethyl acetate, n-propyl acetate, i-propyl acetate, n-butyl acetate, i-butyl acetate, t-butyl acetate, n-amyl acetate, i-amyl acetate, sec-amyl acetate, t-amyl acetate, n-butyl propionate, ethyl butyrate, i-propyl butyrate, methyl isobutyrate, ethyl isobutyrate, methyl valerate, ethyl isovalerate, ethyl pivalate and the like. Ethyl acetate is more preferable.

When the solvent is a mixture, the ratio of the mixed solvents is not limited, but the reaction may be conducted at an optionally ratio of the mixed solvents.

The amount of the solvent is not also limited, but generally, it ranges from 1 to 100 ml, more preferably from 5 to 50 ml, further preferably from 10 to 30 ml per 1 g of thioether (I).

The reaction temperature is not also limited, but generally, the reaction is conducted at −50° C. to room temperature, more preferably at −40° C. to 10° C. in the embodiment a) and at −30° C. to 20° C. in the embodiment b), further preferably at −30° C. to 0° C. in the embodiment a) and at −20° C. to 10° C. in the embodiment b).

The sequence of adding the each reagent (raw material) for the reaction is not also limited, but the following sequence, for example, can bring about more preferable results.

Embodiment a):

1. A perborate is suspended in a solvent, followed by the dropwise addition of an acid anhydride and stirring to prepare a homogeneous mixture, to which is added a solvent if necessary. The resulting solution is added dropwise into a solution of thioether (I).

2. A perborate is added to and dissolved in an acid anhydride and a solvent, and the resulting solution is added dropwise into a solution of thioether (I).

3. A perborate is added to and dissolved in a mixture solution of an acid anhydride and a solvent, and the resulting solution is added dropwise into a solution of thioether (I).

4. A perborate is suspended in a solvent, followed by the dropwise addition of a mixture solution of an acid anhydride and a solvent. Then, the resulting solution is stirred to prepare a homogenous solution, which is then added dropwise into a solution of thioether (I).

5. A perborate is dissolved in a solvent, and the resulting solution is added dropwise into a solution of thioether (I) and a metal catalyst.

6. A metal catalyst is added to a solution of thioether (I), followed by the dropwise addition of a solution of a perborate.

Embodiment b):

1. A base is added to a solution or suspension of thioether (I), to which is then added N-halosuccinimide at low temperature, followed by stirring.

2. A solution of thioether (I) and a base is added to a solution of N-halosuccinimide at low temperature, followed by stirring.

3. A base solution is added dropwise into a solution of thioether (I) and N-halosuccinimide.

4. A base is added to a solution of thioether (I), followed by the addition of 1,3-dihalo-5,5-dimethylhydantoin at low temperature and stirring.

5. A solution of thioether (I) and a base is added to a solution of 1,3-dihalo-5,5-dimethylhydantoin at low temperature, followed by stirring.

6. A base solution is added dropwise into a solution of thioether (I) and 1,3-dihalo-5,5-dimethylhydantoin, followed by stirring.

7. A base is added to a solution of thioether (I), followed by the addition of a dichloroisocyanurate and subsequent stirring.

8. A solution of thioether (I) and a base is added to a solution of a dichloroisocyanurate at low temperature, followed by stirring.

9. A base solution is added dropwise into a solution of thioether (I) and a dichloroisocyanurate, followed by stirring.

In the practice of the procedures (1) to (9) described above, more preferable results can be observed by confirming that the pH of the reaction solution is always at basicity, more preferably at pH 12 or higher, under monitoring.

The reaction time varies, depending on the amount of the solvent used, the reaction temperature, the amount of a perborate used in the embodiment a), and the type and amount of an oxidant used in the embodiment b), but generally, the reaction is completed in about 30 min to 6 hr.

The treatment after the completion of the reaction is not also limited, and for example, sodium hydrosulfite and additionally adding reducing agents such as sodium hyposulfite and sodium thiosulfate in the embodiment b) to decompose excess reagents and, if necessary, adjusting the pH of the aqueous layer and the aqueous layer is extracted with the solvent. In the embodiment b), furthermore, the mixture is evaporated, or the resulting crystals are collected by filtration.

The resulting sulfoxide (II) can be purified by conventional methods such as crystallization, recrystallization, column chromatography and the like.

If necessary, the sulfoxide (II) may be converted into a salt according to known methods.

Furthermore, Tetrahedron Letters, 29(24), 2967-2968, 1988 discloses a reaction comprising oxidation of olefin with sodium perborate . tetrahydrate in the presence of an acetic anhydride in methylene chloride, to give epoxide or α,β-diol monoacetate, however the reaction is totally different from the reaction of the present invention comprising oxidation of thioether to give sulfoxide.

JP-A 54-141783 (EP-5129, U.S. Pat. No. 4,255,431) describes that the following oxidants can be used for the oxidation of thioether into sulfoxide; nitric acid, hydrogen peroxide, peracid, perester, ozone, dinitrogen tetraoxide, iodobenzene, 1-chlorobenzotriazole, tert-butyl hypochlorite, a complex of diazo-bicyclo[2,2,2]octane with bromine, sodium metaperiodate, selenium dioxide, manganese dioxide, chromic acid, ceric ammonium nitrate, bromine, chlorine and sulfuryl chloride, as well as N-halosuccinimide. However, m-chloroperbenzoic acid which is a peracid is the only one specifically disclosed in the Examples of the above-mentioned JP-A 54-141783. Any description that only N-halosuccinimide is specifically excellent among the above various oxidants is never found in the entirety of the specification or any description suggesting the excellency is absolutely never found therein. Further, any description that the presence of a base is essential or preferable is absolutely never found therein.

Accordingly, the description about oxidants in JP-A 54-141783 is regarded as a mere example of general oxidants, with no influence on the novelty of the present invention.

In J. O. C., 33(10), 3976-7, 1968, the reaction which relates to the oxidation of sulfide (thioether) with N-halosuccinimide is described. However, the sulfide specifically disclosed in the reference includes only six compounds, namely dimethyl sulfide, diethyl sulfide, di-n-propyl sulfide, dibenzyl sulfide, benzyl phenyl sulfide and diphenyl sulfide, and is entirely different from the thioether (I) of the present invention in structure.

Figure 1:
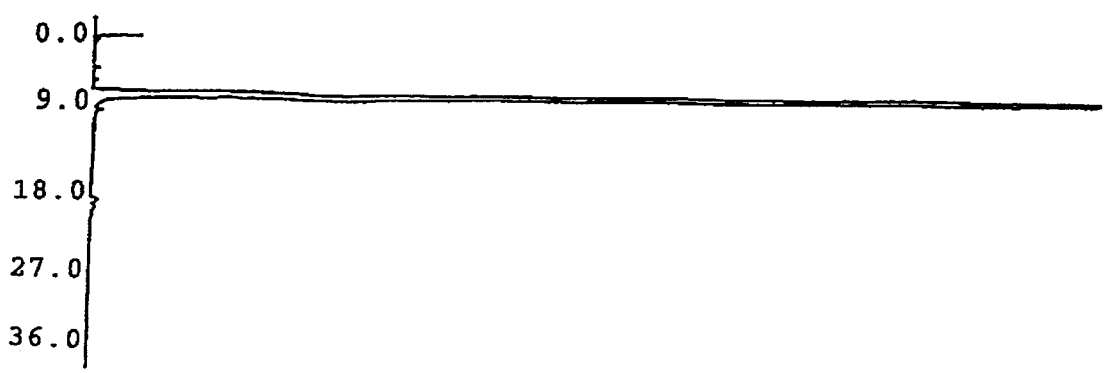
FIG. 1 is an HPLC chart showing that the 2-{[4-(3-methoxypropoxy)-3-methylpyridin-2-yl]methylsulfinyl}-1H-benzimidazole (Rabeprazole free base) obtained in Example 1 has a high purity.

Consequently, to describe the present invention more in detail, Examples and Referential Examples will be given below. However, it is needless to say that the present invention is not limited thereto.

EXAMPLES

Example 1

Synthesis of 2-{[4-(3-methoxypropoxy)-3-methylpridin-2-yl]methylsufinyl}-1H-benzimidazole (Rabeprazole free base)

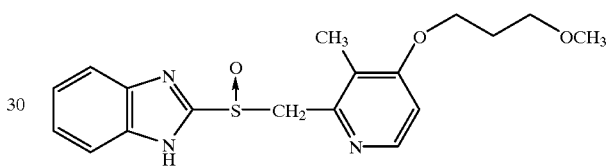

Sodium perborate 4H$_2$O (tetrahydrate) (3.06 g, 18.9 mmol, 97%) was suspended in water (8 ml), and then, acetic anhydride (1.84 ml, 18.9 mmol, 95%) was added dropwise thereto while the bulk temperature of the mixture was kept at 20° C. The resulting mixture was then stirred for about 5 min, to prepare a homogenous solution. Methanol (8 ml) was further added thereto. The resulting solution was added dropwise into a solution (55 ml) of 2-{[4-(2-methoxypropoxy)-3-methylpyridin-2-yl]methylthio}-1H-benzimidazole (referred to as Compound I hereinafter; 5.0 g, 14.6 mmol) in toluene/methanol (10:1) at −20° C. over about 30 min, and the resulting mixture was continued stirring at the same temperature. After about 2 hr, the completion of the reaction was confirmed by HPLC. 10 ml of an aqueous 0.1 wt % sodium hydrosulfite solution was added to the resulting reaction mixture and then, it was continuously stirred at the same temperature for 10 min. The reducibility of the mixture was confirmed with potassium iodide starch paper, followed by adding a 2 M aqueous solution of sodium hydroxide (10 ml) to adjust the solution to pH 8. The aqueous layer and the organic layer was separated and then, the aqueous layer was extracted with 20 ml of toluene. The organic layer was washed with 15 ml of brine. The resulting organic layer was evaporated to a final volume of 25 ml, followed by the addition of ethyl acetate (20 ml), and the resulting solution was stirred at −20° C. for 1 hr to crystallize. The resulting precipitates were filtered under reduced pressure, washed twice with 5 ml of toluene/ethyl acetate (1:1) solution pre-cooled to −20° C., and dried under reduced pressure for 1 hr, to give the title compound (4.37 g, yield; 83.6%) as a white solid.

$^1$H-NMR (400 MHz, CDCl$_3$); δ (ppm) 1.83–2.09(s, 3H), 2.13(s, 3H), 3.34(s, 3H), 3.52(t,J=6.2 Hz, 2H), 4.05(t,J−6.2

Hz, 2H), 4.79(s, 2H), 6.70(d,J=5.7 Hz, 1H), 7.07–7.30(m, 2H), 7.30–7.60 (br-s, 2H), 8.27(d,J=5.7 Hz, 1H).

Example 2

Synthesis of 2-{[4-(3-methoxypropoxy)-3-methylpyridin-2-yl]]methylsulfinyl}-1H-benzimidazole (Rabeprazole free base)

Sodium perborate.$4H_2O$ (2.12 g, 13.8 mmol) was dissolved in 10 ml of water/methanol (1:1) solution containing of acetic anhydride (1.28 ml, 13.8 mmol). The resulting solution was added dropwise into 66 ml of a solution of the Compound I (3.0 g, 8.73 mmol) in toluene/methanol (10:1) at −5° C. over about 40 min, and then the resulting mixture was stirred as it was at the same temperature. The reaction was followed by HPLC. 1.5 hr after the dropwise addition, a 0.1 wt % aqueous solution of sodium hydrosulfite solution (10 ml) was added thereto, and the resulting mixture was stirred as it was at the same temperature for 10 min. The reductive activity of the solution was confirmed with potassium iodide starch paper followed by adding a 2 M aqueous solution of sodium hydroxide (8.6 ml) to adjust the solution to pH 8 and adding 40 ml of water. After separating the aqueous layer and the organic layer, the resulting organic layer was washed with water (20 ml). And then, it was evaporated to a final volume of 15 ml, 15 ml of ethyl acetate was added thereto, and the resulting mixture was stirred at −20° C. for 30min to crystallize. The resulting precipitates were filtered under reduced pressure, washed with 10 ml of toluene/ethyl acetate (1:1) pre-cooled to −20° C., and dried under reduced pressure, to give the title compound (2.55 g, yield: 81.3%) as a white solid.

Example 3

Synthesis of 2-{[4-(3-methoxypropoxy)-3-methylpyridin-2-yl]methylsulfinyl}-1H-benzimidazole (Rabeprazole free base)

Sodium perborate $4H_2O$ (2.68 g, 17.42 mmol) was dissolved in a solution (10 ml) of water/methanol (1:1) containing acetic anhydride (1.60 ml, 17.46 mmol). The resulting solution was added dropwise into a solution (66 ml) of the Compound I (3.0 g, 8.73 mmol) in toluene/methanol (10:1) at −5° C. over 24 min and the resulting mixture was continued stirring as it was at the same temperature. After about 30 min, the completion of the reaction was confirmed by HPLC. Subsequently, the same procedures as in the previous Example were conducted to give the title compound (2.45 g, yield; 78.2%) as a white solid.

Example 4

Synthesis of 2-{[4-(3-methoxypropoxy)-3-methylpyridin-2-yl]methylsulfinyl}-1H-benzimidazole (Rabeprazole free base)

Sodium perborate.$4H_2O$ (3.35 g, 21.78 mmol) was dissolved in a solution (10 ml) of water/methanol (1:1) containing acetic anhydride (4.4 ml, 45.3 mmol). The resulting solution was added dropwise into a solution (66 ml) of the Compound I (3.0 g, 8.73 mmol) in toluene/methanol (10:1) at −5° C. over 60 min and the resulting mixture was continued stirring as it was at the same temperature. About 2 hr later, the completion of the reaction was confirmed by HPLC. Subsequently, the same procedures as in the previous Example were conducted to give the title compound (2.48 g, yield; 79.4%) as a white solid.

Example 5

Synthesis of 2-{[4-(3-methoxypropoxy)-3-methylpyridin-2-yl]methylsulfinyl}-1H-benzimidazole (Rabeprazole free base)

Sodium perborate.$4H_2O$ (3.06 g, 18.9 mmol) was dissolved in a mixture of acetic anhydride (1.84 ml, 18.9 mmol)/water (8 ml). The resulting solution was added dropwise into a solution (67 ml) of the Compound I (5.0 g, 14.6 mmol) in toluene/dimethylformamide (3:1) mixture at −20° C. over 60 min. The resulting mixture was then stirred as it was at the same temperature. After about 2.5 hr, the completion of the reaction was confirmed by HPLC. Subsequently, the same procedures as in the previous Example were effected to obtain the title compound (4.26 g, yield; 81.5%) as a white solid.

Example 6

Synthesis of 2-{[4-(3-methoxypropoxy)-3-methylpyridin-2-yl]methylsulfinyl}-1H-benzimidazole (Rabeprazole free base)

Sodium perborate.$4H_2O$ (3.06 g, 18.9 mmol) was dissolved in a mixture of acetic anhydride (1.84 ml, 18.9 mmol)/water (8 ml). The resulting solution was added dropwise into a solution (60 ml) of the Compound I (5.0 g, 14.6 mmol) in toluene/ethanol (5:1) at −20° C. over 50 minutes. The resulting mixture was then stirred as it was at the same temperature. After about 2 hr, the completion of the reaction was confirmed by HPLC. Subsequently, the same procedures as in the previous Example were conducted to give the title compound (3.99 g, yield; 78.5%) as a white solid.

Example 7

Synthesis of 2-{[4-(3-methoxypropoxy)-3-methylpyridin-2-yl]methylsulfinyl}-1H-benzimidazole (Rabeprazole free base)

Sodium perborate.$4H_2O$ (30.6 g, 0.189 mol, 97%) was suspended in 80 ml of water. A mixture of acetic anhydride (18.4 ml, 0.189 mol, 95%) and methanol (30 ml) was added dropwise thereto over about 20 min, while the bulk temperature of the mixture was kept at about 15° C. Then, the resulting mixture was stirred for about 10 min, to prepare a homogenous solution. The solution was added dropwise into a solution (550 ml) of the Compound I (50.0 g, 0.146 mol) in toluene/methanol (10:1) at −20° C. over about 2.5 hr, and the resulting mixture was stirred as it was at the same temperature for about 2 hr. The completion of the reaction was confirmed by HPLC. A solution of sodium hydrosulfite (5.5 g) in water (50 ml) was added thereto, and then stirred as it was at the same temperature for 10 min. The reducibility of the solution was confirmed with potassium iodide starch paper, followed by adding a 2 M aqueous solution of sodium hydroxide (110 ml) was added thereto to adjust the solution to pH 8. Ethyl acetate (300 ml), water (200 ml) and methanol (80 ml) were added thereto to separate the aqueous layer and the organic layer. The organic layer was washed with 150 ml of brine and then evaporated on a water bath at a temperature of 30° C. 150 ml of ethyl acetate and 150 ml of toluene were added to the resulting residue to dissolve the residue, and the resulting solution was stirred at −20° C. for 1 hr. The resulting precipitates were filtered under reduced pressure, washed with t-butyl methyl ether (50 ml) for three times, and then dried under reduced pressure for 1 hr to give the title compound as a white powder (48.0 g, yield; 91.8%, an HPLC purity; 95.9%).

Conditions for HPLC Analysis

Solid phase: NUCLEOSIL$_5$C$_{18}$
Mobile phase: MeOH: phosphate buffer (pH 7)=3:2
Flow rate: 1.0 ml/min
Detector: UV detector (290 nm)

Example 8

Synthesis of 2-{[4-(3-methoxypropoxy)-3-methylpyridin-2-yl]methylsulfinyl}-1H-benzimidazole (Rabeprazole free base)

Sodium perborate.4H$_2$O (3.06 g, 18.9 mmol) was suspended in 8 ml of water, followed by the dropwise addition of propionic anhydride (2.56 ml, 18.9 mmol) over 3 min, and the resulting mixture was then stirred for about 10 min, to prepare a homogenous mixture. 8 ml of methanol was added to the resulting mixture (at a bulk temperature of 22.6° C. to 26.2° C.) and then, it was added dropwise into a solution (55 ml) of the Compound I (5.00 g, 14.6 mmol) in toluene/methanol (10:1) at −20° C. over 35 min. The resulting mixture was further stirred at the same temperature for 1 hr. The same procedures as in the previous Example were effected to obtain the title compound (4.19 g, yield; 80.1%).

Example 9

Synthesis of 2-{[3-methyl-4-(2,2,2-trifluoroethoxy)pyrid-2-yl]methylthio}-benzimidazole (Lansprazole)

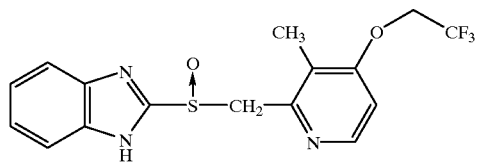

Sodium perborate.4H$_2$O (0.58 g, 3.68 mmol) was dissolved in a mixture of acetic anhydride (0.365 ml, 3.68 mmol) and water (8 ml). The resulting solution was added dropwise to a solution (30 ml) of 2-{[3-methyl-4-(2,2,2-trifluoroethoxy)pyrid-2-yl]methylthio}benzimidazole (1.0 g, 2.83 mmol) in toluene/methanol (5:1) at 0° C. over 16 min. The resulting mixture was continued stirring as it was at the same temperature. After about 1.5 hr later, the completion of the reaction was confirmed by HPLC. After stirring the mixture for further 1 hr, the bulk temperature was gradually raised to 10° C. and the resulting mixture was continued stirring for 4 hr. Then, the mixture was cooled to −15° C. and stirred for 20 min. The resulting crystals were collected by filtration under reduced pressure. The crystals were washed with cooled toluene (10 ml) for two times, and then dried under reduced pressure to give the title compound (0.82 g, yield; 78.4%)as a white powder.

M.p.: 170–172° C. (decomp.) $^1$H-NMR (400 MHz, CDCl$_3$); δ (ppm) 2.20(s, 3H), 4.80(s, 2H), 4.88(s, 2H), 6.98(d,J=5.6 Hz, 1H), 7.33–7.36(m, 2H), 7.63(br-s, 2H), 8.18(d,J=5.6 Hz, 1H).

Example 10

Synthesis of 5-methoxy-2-[(4-methoxy-3,5-dimethyl- 2-pyridyl)methylsulfinyl]-1H-benzimidazole (Omeprazole)

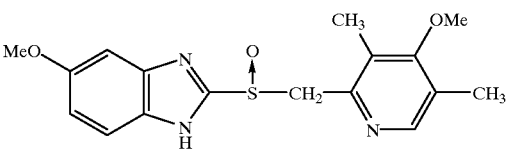

Sodium perborate 4H$_2$O (11.2 g, 73.0 mmol) was suspended in water (50 ml), followed by the dropwise addition of a solution of acetic anhydride (6.87 ml, 73.0 mmol)/methanol (5.75 ml) at 15.4° C. over 6 minutes and then, the mixture was stirred for about 13 min to prepare a homogenous solution (bulk temperature; 15.4° C. to 19.4° C.). The resulting solution was added dropwise to a solution (220 ml) of 5-methoxy-2-[(4-methoxy-3,5-dimethyl-2-pyridyl)methylthio]-1H-benzimidazole (20.0 g, 60.8 mmol) in toluene/methanol (10:1) at −20° C. over 2 hr. The resulting mixture was further stirred at the same temperature for 1 hr. The resulting crystals were collected by filtration, washed for three times with water (20 ml) and washed twice with tert-butyl methyl ether (20 ml). The resulting crystals were dried, to give the title compound (17.8 g, yield; 85.0%) as a white solid.

$^1$H-NMR (400 MHz, CDCl$_3$); δ ppm) 2.20(s, 3H), 2.25(s, 3H), 3.68(s, 3H), 3.86(s, 3H), 4.70(Abq, 2H, J=13.7 Hz), 6.98–7.00(m, 2H), 7.65(br-d, 1H, J=8.29 Hz), 8.24(s, 1H), 1.19(br-s, 1H).

Example 11

Synthesis of 2-{[4-(3-methoxypropoxy)- 3-methypyridin-2-yl]methylsulfinyl}-1H-benzimidazole (Rabeprazole free base)

Sodium perborate.4H$_2$O (537 mg, 3.49 mmol) was dissolved in a mixture of acetic anhydride (0.40 ml, 6.99 mmol) and water (10 ml). The resulting solution was added dropwise into a mixture (21ml) of the compound I (1.00 g, 2.91 mmol) and vanadyl acetylacetonate ((CH$_3$COCHCOCH$_3$)$_2$VO, 77.3 mg, 0.29 mmol) in methanol/toluene (20:1) at 4° C. over 40 min, and the resulting mixture was continued stirring as it was at the same temperature. After about 40 min, the completion of the reaction was confirmed by HPLC, and subsequently, the same procedures as in the previous Example were conducted to give the title compound (2.35 g, yield; 75.0%).

Example 12

Synthesis of 2-{[4-(3-methoxypropoxy)-3-methylpyridin-2-yl]methylsulfinyl}-1H-benzimidazole (Rabeprazole free base)

Sodium perborate.4H$_2$O (1.61 g, 10.5 mmol) was dissolved in a mixture of acetic acid (1.20 ml, 21.0 mmol) and water (30 ml). The resulting solution was added dropwise into a mixture solution (63ml) of the compound I (3.00 g, 2.91 mmol) and vanadyl acetylacetonate (232 mg, 0.87 mmol) in methanol/toluene (20:1) at −5° C. over about 1 hr, and the resulting mixture was continued stirring as it was at the same temperature. After about 5 hr, the completion of the reaction was confirmed by HPLC. Subsequently, the resulting mixture was treated by the same procedures as in the previous Example to give the title compound (2.22 g, yield; 71.0%).

Examples 13 to 21

Oxidation with N-halosuccinimide

Examples 22 to 25

Oxidation with 1,3-Dihalo-5,5-dimethydantoin

Example 26

Oxidation with Dichloroisocyanurate
Condition for HPLC Analysis
Solid phase: NUCLEOSIL$_5$C$_{18}$(4.6 mm I.D×150 mm, 5 μm)
Mobile phase: MeOH/0.05M phosphate buffer (pH 7)=3:2
Flow rate: 1.0 ml/min
Temperature: 25° C.
Detector: UV detector at 290 nm Example 13

Synthesis of 2-{[4-(3-Methoxypropoxy)-3-methylpyridin-2-yl]methylsulfinyl}-1H-benzimidazole (Rabeprazole free base)

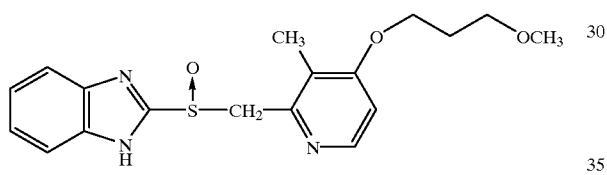

2-{[4-(3-Methoxypropoxy)-3-methylpyridin-2-yl]methylthio}-1H-benzimidazole (5.0 g 14.6 mmol; referred to as Compound I hereinafter) was dissolved in 20 ml of N,N-dimethylformamide, followed by the addition of a 2N aqueous solution of sodium hydroxide (18 ml). A solution (10 ml) of N-chlorosuccinimide (2.71 g, 20.3 mmol) in N,N-dimethylformamide was added dropwise to the solution at −20° C. to −10° C. The reaction mixture was reacted at −15° C. to −7° C. for 1.5 hr. To the reaction mixture was added a 10% aqueous solution of sodium thiosulfate (5 ml), stirred for 2 min and then, a solution (60 ml) of ammonium acetate (23.1 g) in water was added thereto. 60 ml of ethyl acetate and 10 g of sodium chloride were added thereto to extract the reaction mixture, and the aqueous layer was further extracted with ethyl acetate (40 ml). The organic layers were combined, washed with a 15% aqueous solution of sodium chloride (80 ml) for three times and then, the solvent was evaporated. To the resulting oil was added 12 ml of ethyl acetate, 28 ml of hexane and 10 ml of toluene, followed by stirring at room temperature for 1 hr. The resulting crystals were collected by filtration, washed with a solvent mixture (10 ml) of 30% ethyl acetate and hexane for two times and then, dried under reduced pressure, to give the title compound (4.7 g, yield; 90.6%) as grayish white crystals.
$^1$H-NMR (400 MHz, DMSO-d$_6$); δ (ppm) 1.10(t,J=7.2 Hz, 3H), 2.13(s, 3H), 3.50(q,J=7.2 Hz, 2H), 3.71(m, 2H), 4.16(m, 2H), 4.70(d,J=13.6 Hz, 1H), 4.78(d,J=13.6 Hz, 1H), 6.96(d,J5.6 Hz, 1H), 7.28(m, 2H), 7.62(m, 2H), 8.20(d,J=5.6 Hz, 1H).

Example 14

Synthesis of 2-{[4-(3-methoxypropoxy)-3-methylpyridin-2-yl]methylsulfinyl}-1H-benzimidazole) (Rabeprazole free base)

The Compound I (5.0 g, 14.6 mmol) was suspended in 20 ml of acetonitrile, followed by the addition of a 2N aqueous solution of sodium hydroxide (14.5 ml). To the resulting solution was added dropwise a solution (8 ml) of N-chlorosuccinimide (2.13 g, 16.0 mmol) in N,N-dimethylformamide at −18 ° C. to −8 ° C. The reaction mixture was reacted at −15° C. to −0° C. for 1.5 hr. To the reaction mixture was added a 10% aqueous solution of sodium thiosulfate (5 ml), and stirred for 2 min, followed by the addition of a solution (60 ml) of ammonium acetate (10 g) in water. Ethyl acetate (60 ml) and sodium chloride (10 g) were added thereto to extract, and further the aqueous layer was extracted with ethyl acetate (40 ml). The organic layers were combined, washed with a 15% aqueous solution of sodium chloride (80 ml) for three times, and then the solvent was evaporated. Ethyl acetate (12 ml), hexane (28 ml) and toluene (12 ml) were added to the resulting oil, and the resulting mixture was stirred at room temperature for 1 hr. The resulting crystals were collected by filtration, washed with a solvent mixture (10 ml) of 30% ethyl acetate and hexane for two times, and then dried under reduced pressure, to give the title compound (4.68 g, yield; 90.0%) as white crystals.

Example 15

Synthesis of 2-{[4-(3-methoxypropoxy)-3-methylpyridin-2-yl]methylsulfinyl}-1H-benzimidazole (Rabeprazole free base)

The Compound I (5.0 g, 14.6 mmol) was suspended in a solvent mixture of toluene (20 ml) and acetonitrile (10 ml), followed by the addition of a 2N aqueous solution of sodium hydroxide (14.5 ml). To the resulting solution was added dropwise a solution (8 ml) of N-chlorosuccinimide (2.13 g, 16.0 mmol) in N,N-dimethylformamide at 0° C. to 9° C. The reaction mixture was reacted at 0° C. to 15° C. for 1.5 hr. To the reaction mixture was added a 10% aqueous solution of sodium thiosulfate (5 ml) and stirred for 2 min, followed by the addition of a 2N aqueous solution of sodium hydroxide (14.5 ml). After adding toluene (10 ml) thereto to separate the organic layer, acetic acid (2.2 ml) was added to the aqueous layer to adjust it to pH 8.5. Ethyl acetate (60 ml) and sodium chloride (5 g) were added thereto to extract and further the aqueous layer was extracted with ethyl acetate (40 ml). The organic layers were combined, washed with a 15% aqueous solution of sodium chloride (80 ml) for three times and then the solvent was evaporated. Ethyl acetate (10 ml), toluene (10 ml) and t-butyl methyl ether (20 ml) were added to the resulting oil and the mixture was stirred at room temperature for 1 hr. The resulting crystals were collected by filtration, washed with t-butyl methyl ether (10 ml) for two times, and then dried under reduced pressure, to give the title compound (3.9 g, yield; 74.8%) as grayish white crystals.

Example 16

Synthesis of 2-{[4-(3-methoxypropoxy)-3-methylpyridin-2-yl]methylsulfinyl}-1H-benzimidazole (Rabeprazole free base)

The Compound I (5.0 g, 14.6 mmol) was suspended in 20 ml of tetrahydrofuran, followed by the addition of a 2N aqueous solution of sodium hydroxide (14.5 ml). To the resulting solution was added dropwise a solution (8 ml) of N-chlorosuccinimide (2.13 g, 16.0 mmol) in N,N-dimethylformamide at 0° C. to 9° C. The reaction mixture was reacted at 5° C. to 0 ° C. for 1 hr. To the reaction mixture was added 5 ml of a 10% aqueous solution (5 ml) of sodium thiosulfate was added to the reaction mixture and stirred for 2 min, followed by the addition of a 2N aqueous solution (14.5 ml) of sodium hydroxide. 40 ml of toluene was added to separate the organic layer, 2.2 ml of acetic acid was added to the aqueous layer to adjust it to pH 8.5. Ethyl acetate (60 ml) and sodium chloride (4 g) were added thereto to extract and further the aqueous layer was extract with ethyl acetate (40 ml). The organic layers were combined, washed with a 15% aqueous solution of sodium chloride (80 ml) for three times, and then the solvent was evaporated. Ethyl acetate (10 ml), toluene (10 ml) and t-butyl methyl ether (20 ml) were added to the resulting oil, and stirred at room temperature for 1 hr. The resulting crystals were collected by filtration, washed with t-butyl methyl ether (10 ml) for two times, and then dried under reduced pressure, to give the title compound (3.9 g, yield; 74.8%) as grayish white crystals.

Example 17

Synthesis of 2-{[4-(3-methoxypropoxy)-3-methylpyridin-2-yl]methylsulfinyl}-1H-benzimidazole (Rabeprazole free base)

The Compound I (5.0 g, 14.6 mmol) was suspended in 20 ml of acetonitrile, followed by the addition of a 2N aqueous solution of sodium hydroxide (14.5 ml). To the resulting solution was added dropwise a solution (8.5 ml) of N-chlorosuccinimide (2.32 g, 17.4 mmol) in N,N-dimethylformamide at −5° C. to 5° C. During the dropwise addition, the pH of the reaction mixture was monitored, and a 2N aqueous solution of sodium hydroxide (10 ml) was simultaneously added dropwise thereto so as not to lower the pH value of the reaction solution below pH 12. After the completion of the dropwise addition, the mixture was reacted for further 45 min at −3° C. to 0° C. After adding a 10% aqueous solution of sodium thiosulfate (10 ml) to the reaction mixture and stirring the mixture for 2 min, water (60 ml) was added thereto. The resulting mixture was adjusted to pH 9.2, by adding about 2.5 ml of acetic acid thereto, followed by the addition of ethyl acetate (60 ml) and sodium chloride (12 g) to extract. Further, the aqueous layer was extracted with ethyl acetate (40 ml). The organic layers were combined, washed with a 15% aqueous solution of sodium chloride (80 ml) for three times, and then the solvent was evaporated. Ethyl acetate (12 ml), hexane (28 ml) and toluene (10 ml) were added to the resulting oil, and the mixture was stirred at room temperature for 1 hr. The resulting crystals were collected by filtration, washed with a solvent mixture (10 ml) of 30% ethyl acetate and hexane for two times, and the dried under reduced pressure, to give the title compound (4.76 g, yield; 91.3%) as grayish white crystals.

Example 18

Synthesis of 2-{[4-(3-methoxypropoxy)-3-methylpyridin-2-yl]methylsulfinyl}-1H-benzimidazole (Rabeprazole free base)

The Compound I (5.0 g, 14.6 mmol) was suspended in 20 ml of acetonitrile, followed by the addition of a 2N aqueous solution of sodium hydroxide (14.5 ml). To the resulting solution was added dropwise 8.5 ml of a solution of N-chlorosuccinimide (2.32 g, 17.4 mmol) in N,N-dimethylformamide at −5° C. to 5° C. During the dropwise addition, the pH of the reaction solution was monitored, and 10 ml of a 2N aqueous solution of sodium hydroxide (10 ml) solution was simultaneously dropwise added to the reaction solution so as not to lower the pH value of the reaction solution below pH 12. After the termination of the dropwise addition, the reaction solution was reacted at −3° C. to 0° C. for further 45 min. To the reaction mixture was added a 10% aqueous solution of sodium thiosulfate (10 ml), stirred for 2 min and then, the acetonitrile was evaporated. The resulting solution was adjusted to pH 9.1, by adding 85 ml of water and about 1.2 ml of acetic acid to the solution, followed by stirring at 4° C. for 12 hr. The resulting crystals were collected by filtration, washed with water (20 ml) for three times and dried under reduced pressure, to give the title compound (3.97 g, yield; 76.2%) as grayish white crystals.

Example 19

Synthesis of 2-{[4-(3-methoxypropoxy)-3-methylpyridin-2-yl]methylsulfinyl}-1H-benzimidazole (Rabeprazole free base)

The Compound I (5.0 g, 14.6 mmol) was suspended in 20 ml of acetonitrile, followed by the addition of a 2N aqueous solution of sodium hydroxide (14.5 ml). To the resulting solution was added dropwise 8.5 ml of a solution of N-chlorosuccinimide (2.32 g, 17.4 mmol) in N,N-dimethylformamide at −5° C. to 5° C. During the dropwise addition, the pH of the reaction solution was monitored, and a 2N aqueous solution of sodium hydroxide (10 ml) was simultaneously dropwise added to the reaction solution so as not to lower the pH value of the reaction solution below pH 12. After the completion of the dropwise addition, the reaction solution was reacted at −3° C. to 0° C. for further 45 min. To the reaction mixture was added a 10% aqueous solution of sodium thiosulfate (10 ml), stirred for 2 min and then, 60 ml of water was added thereto. The resulting solution was adjusted to pH 9.2, by adding about 1.3 ml of acetic acid to the solution, followed by the addition of 50 ml of isopropyl acetate and 50 ml of hexane. Then, the resulting mixture was stirred at 4° C. for 12 hr. The resulting crystals were collected by filtration, washed with 10 ml of a solvent mixture of 30% isopropyl acetate and hexane, and dried under reduced pressure, to give the title compound (3.47 g, yield; 66.6%) as grayish white crystals.

Example 20

Synthesis of 2-{[4-(3-methoxypropoxy)-3-methylpyridin-2-yl]methylsulfinyl}-1H-benzimidazole (Rabeprazole free base)

The Compound I (15.0 g, 43.7 mmol) was suspended in 75 ml of acetonitrile, followed by the addition of 75 ml of a 2N aqueous solution of sodium hydroxide. To the resulting solution was added dropwise N-chlorosuccinimide (6.42 g, 48 mmol) little by little at −5° C. The reaction mixture was reacted at −5° C. for 1.5 hr. To the reaction mixture was added 5 ml of a 1 H aqueous solution of sodium thiosulfate solution, followed by stirring for 2 min and washing with toluene (10 ml) for two times. Subsequently, 4.2 g of formic acid was added to the aqueous layer at 5° C., to adjust the aqueous layer to pH 9.0. The resulting mixture was stirred as it was at the same temperature for about 15 hr, and then the resulting slurry was filtered. The resulting solid was dried, to give the title compound (14.00 g, yield; 89.2%, purity; 99.8%) as white crystals

Example 21

Synthesis of 2-{[3-methyl-4-(2,2,2-trifluoroethoxy)pyridin-2-yl]methylsulfinyl}-1H-benzimidazole (Lansoprazole)

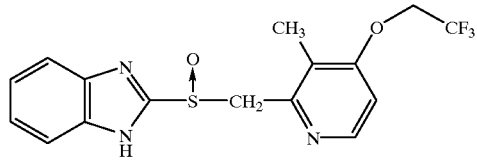

2-{[3-Methyl-4-(2,2,2-trifluoroethoxy)pyridin-2-yl]methylthio}-1H-benzimidazole (1.0 g, 2.83 mmol) was suspended in 8 ml of acetonitrile, followed by the addition of 3.5 ml of a 2N aqueous solution of sodium hydroxide. A solution (2 ml) of N-chlorosuccinimide (453 mg, 3.40 mmol) in N,N-dimethylformamide was added dropwise to the solution at −4° C. to 3° C. The reaction mixture was subsequently reacted at −3° C. to 0° C. for 1.5 hr. To the reaction mixture was added a 10% aqueous solution of sodium thiosulfate (2 ml) was added to the reaction mixture and the resulting mixture was stirred for 2 min, followed by the addition of water (20 ml) and acetic acid (0.4 ml) to adjust the solution to about pH 8.5. Ethyl acetate (20 ml) and sodium chloride (3 g) were added thereto to extract and the aqueous layer was further extracted with ethyl acetate (10 ml). The organic layers were combined, washed with a 15% aqueous solution of sodium chloride (10 ml) for three times, and the solvent was evaporated. Ethyl acetate (3 ml), hexane (7 ml) and toluene (2.5 ml) were added to the resulting oil, and then stirred at room temperature for 1 hr. The resulting crystals were collected by filtration, washed with a solvent mixture (3 ml) of 30% ethyl acetate and hexane for two times, and then dried under reduced pressure, to give the title compound (0.88 g, yield; 84.1%) as grayish white crystals. $^1$H-NMR (400 MHz, DMSO-$d_6$); δ (ppm) 2.16(s, 3H), 4.74(d,J=13.7 Hz, 1H), 4.87(d,J=13.7 Hz, 1H), 4.88(d,J=8.8 Hz, 1H), 4.91(d,J=8.8 Hz, 1H), 7.08(d,J=5.9 Hz, 1H), 7.29 (m, 2H), 7.56(m, 1H), 7.70(m, 1H), 8.27(d,J=5.9 Hz, 1H), 13.55(s, 1H).

Example 22

Synthesis of 2-{[4-(3-methoxypropoxy)-3-methylpyridin-2-yl]methylsulfinyl}-1H-benzimidazole (Rabeprazole free base)

The Compound I (10.0 g, 29.1 mmol) was dissolved in 80 ml of dimethylformamide, followed by the addition of a solution of potassium hydrogen carbonate (2.91 g, 29.1 mmol) in water (20 ml). The resulting mixture solution was stirred under ice-cooling. At the same temperature, a solution of 1,3-dichloro-5,5-dimethylhydantoin (4.01 g, 20.37 mmol) in dimethylformamide (15 ml) was added dropwise thereinto over 3 min, and stirred as it was at the same temperature for 70 min. Additionally, 1,3-dichloro-5,5-dimethylhydantoin (0.34 g; 8.73 mmol) was added to the resulting mixture, and then it was stirred for 40 min. An aqueous solution (10 ml) of sodium hyposulfite (5.13 g, 40.74 mmol) was added to the resulting mixture, stirred for 5 min, and then a 2M aqueous solution of sodium hydroxide (6 ml) was added thereto to adjust the solution to pH 8. Water (80 ml) was added thereto, and the resulting aqueous layer was extracted with ethyl acetate (200 ml) for two times and with 100 ml thereof once, and the extracted aqueous layers were combined together. The organic layer was washed with a 10% aqueous solution of brine for two times. The organic layer was evaporated, and to the resulting residue were added ethyl acetate (30 ml), toluene (30 ml) and n-hexane (30 ml), and the resulting mixture was stirred at −15° C. for 11 hr. The resulting crystals were filtered under reduced pressure, washed with t-butyl ethyl ether (25 ml) for two times and then dried to give the title compound (7.33 g, yield; 70.0%, an HPLC purity; 98.9%) as a white solid.

Example 23

Synthesis of 2-{[4-(3-methoxypropoxy)-3-methylpyridin-2-yl]methylsulfinyl}-1H-benzimidazole (Rabeprazole free base)

The Compound I (10.0 g, 29.1 mmol) was dissolved in 80 ml of dimethylformamide, followed by the addition of a solution (20ml) of sodium hydrogen carbonate (2.46 g, 29.2 mmol) in water. The resulting mixture was stirred under ice-cooling. At the same temperature, a solution (20 ml) of 1,3-dichloro-5,5-dimethylhydantoin (4.01 g, 20.37 mmol) in dimethylformamide was added dropwise thereinto over 10 min and stirred at the same temperature for 80 min. Further, 1,3-dichloro-5,5-dimethylhydantoin (115 mg, 0.58 mmol) was added thereto and stirred for 20 min. A 1.0 M aqueous solution of sodium thiosulfate (30 ml) was added thereto and stirred for 5 min. Then, 30 ml of brine was added thereto and the extracted with ethyl acetate (100 ml×2). The organic phase was rinsed in 100 ml of an aqueous 15% sodium chloride solution and in 15 ml thereof and concentrated under reduced pressure. Toluene (15 ml), ethyl acetate (15 ml) and t-butyl methyl ether (15 ml) were added to the resulting residue, and the mixture was stirred at −10° C. for 13 hr. The resulting crystals were filtered under reduced pressure, washed with t-butyl methyl ether (50 ml) for two times, and then dried, to give the title compound (7.05 g, yield; 67.0%) as a white solid.

Example 24

Synthesis of 2-{[4-(3-methoxypropoxy)-3-methylpyridin-2-yl]methylsulfinyl}-1H-benzimidazole (Rabeprazole free base)

The Compound I (5.0 g, 14.5 mmol) was dissolved in 25 ml of ethyl acetate, followed by the addition of a solution of sodium hydrogencarbonate (3.21 g, 32.1 mmol) in water (25 ml). The resulting mixture solution was stirred under ice-cooling. At the same temperature, 1,3-dichloro-5,5-dimethylhydantoin (2.87 g, 14.6 mmol) was added thereto, and then stirred for 2 hr. Additionally, the resulting mixture was stirred at −10° C. for 30 min. The resulting crystals were filtered under reduced pressure, washed with water (10 ml×2) and t-butyl methyl ether (10 ml×2), and then dried, to give the title compound (2.79 g, yield; 53.3%, an HPLC purity; 98.8%) as white crystals.

Example 25

Synthesis of 2-{[4-(3-methoxypropoxy)-3-methylpyridin-2-yl]methylsulfinyl}-1H-benzimidazole (Rabeprazole free base)

The Compound I (10.0 g, 29.1 mmol) was dissolved in 40 ml of ethyl acetate, followed by the addition of a solution of sodium hydrogencarbonate (13.9 g, 140 mmol) in water (55 ml). The resulting mixture was stirred at −5° C. At the same temperature, a solution of 1,3-dichloro-5,5-dimethylhydantoin (6.88 g, 34.92 mmol) in ethyl acetate (60 ml) added thereto. After stirring for 2 hr, a 10% aqueous solution of sodium hydrosulfite (50 ml) was added, and then stirred for 10 min. A mixture solution (110 ml) of n-hexane/toluene (1:1) was added thereto and the resulting mixture was stirred at –20° C. for 1.5 hr. The resulting crystals were collected by filtration, washed with water (50 ml×4) and t-butyl methyl ether (25 ml×2), and then dried, to give the title compound (7.09 g, yield; 68%, an HPLC purity; 98.2%) as white crystals.

Example 26

Synthesis of 2-{[4-(3-methoxypropoxy)-3-methylpyridin-2-yl]methylsulfinyl}-1H-benzimidazole (Rabeprazole free base)

The Compound I (5.0 g, 14.5 mmol) was dissolved in 20 ml of acetonitrile, followed by the addition of a 2M aqueous solution of sodium hydroxide (29.1 ml). The resulting mixture solution was stirred at –15° C. At the same temperature, a solution of sodium dichloroisocyanurate (2.24 g, 10.2 mmol) in water (15 ml) was added dropwise thereinto over 10 min. During the addition, the temperature of the reaction mixture was raised from –15° C. to –5.6° C. After stirring for 15 min at the same temperature, a solution (5 ml) of sodium hydrosulfide (0.50 g) in water was added thereto, stirred for 30 min, and the insoluble matters were filtered off. The filtrate was adjusted to pH 7, by adding about 3 ml of formic acid thereto. The aqueous layer was extracted with ethyl acetate (25 ml) once and with 10 ml thereof once. The organic layer was washed with brine (10 ml) and evaporated. Ethyl acetate (20 ml), toluene (12 ml) and n-hexane (20 ml) were added to the resulting residue, followed by stirring at –15° C. for 11 hr. The resulting crystals were filtered under reduced pressure, washed with t-butyl methyl ether (20 ml) for two times, and then dried, to give the title compound (3.71 g, yield; 70.8%, an HPLC purity; 97.3%) as pale yellowish white crystals.

Next, to show the excellent effect of the present invention, Reference Examples in which the oxidants (nitric acid, sodium metaperiodate) disclosed in JP-A 54-141783 are used as comparative controls, and sodium borate and sodium chlorate are used as other oxidants, to produce the sulfoxide (II) of the present invention.

The oxidants except the above oxidants disclosed in JP-A 54-141783 are disadvantageously unstable, dangerous (explosive), unavailable at large volume and expensive, and cause pollution. Thus, these oxidants are not applicable as industrial raw materials.

REFERENTIAL EXAMPLES

Referential Example 1

Synthesis of 2-{[4-(3-methoxypropoxy)-3-methylpyridin-2-yl]methylsulfinyl}-1H-benzimidazole (Rabeprazole free base)
(oxidant:nitric acid)

The Compound I (2 g, 5.82 mmol) was dissolved in 20 ml of methanol, followed by the dropwise addition of 61% nitric acid (0.6 g, 5.82 mmol) at room temperature. After the dropwise addition, reacting the resulting mixture at room temperature for 2 hr. Subsequently, the change of the reaction mixture was confirmed by TLC (methanol/ethyl acetate=1/6; refer to the same hereinafter). Consequently, no formation of the title compound was observed.

Referential Example 2

Synthesis of 2-{[4-(3-methoxypropoxy)-3-methylpyridin-2-yl]methylsulfinyl}-1H-benzimidazole (Rabeprazole free base)
(oxidant:sodium metaperiodate)

The Compound I (2 g; 5.82 mmol) was dissolved in 50 ml of methanol and the solution was cooled to 0° C. After cooling, sodium metaperiodate (1.26 g, 5.82 mmol) dissolved in water (25 ml) was added dropwise thereto. After the dropwise addition, reacting the mixture at room temperature for 22 hr. Subsequently, the change of the reaction mixture was confirmed by TLC. Consequently, no formation of the title compound was confirmed.

Referential Example 3

Synthesis of 2-{[4-(3-methoxypropoxy)-3-methylpyridin-2-yl]methylsulfinyl}-1H-benzimidazole (Rabeprazole free base)
(oxidant:sodium bromate)

The Compound I (2 g, 5.82 mmol) was dissolved in 30 ml of dioxane, followed by the dropwise addition of sodium bromate (1.69 g, 8.14 mmol) dissolved in water (5 ml). After the dropwise addition, reacting the mixture at room temperature for 1.5 hr. Subsequently, the change of the reaction mixture was confirmed by TLC. Consequently, no formation of the title compound was observed.

Reference Example 4

Synthesis of 2-{[4-(3-methoxypropoxy)-3-methylpyridin-2-yl]methylsulfinyl}-1H-benzimidazole (Rabeprazole free base)
(oxidant:sodium bromate)

The Compound I (2 g, 5.82 mmol) was dissolved in 40 ml of methanol, followed by the dropwise addition of sodium bromate (1.69 g, 8.14 mmol) dissolved in water (20 ml). After the dropwise addition, reacting the mixture at room temperature for 16 hr. Subsequently, the change of the reaction mixture was confirmed by TLC. Consequently, no formation of the title compound was observed.

Referential Example 5

Synthesis of 2-{[4-(3-methoxypropoxy)-3-methylpyridin-2-yl]methylsulfinyl}-1H-benzimidazole (Rabeprazole free base)
(oxidant:sodium chlorate)

The Compound I (5 g, 14.6 mmol) was dissolved in a solvent mixture of ethyl acetate (75 ml), methanol (25 ml) and water (30 ml), followed by the dropwise addition of a 5% aqueous solution of sodium chlorate (22 g, 14.6 mmol) at 5° C. 1 hr after the dropwise addition, the change of the reaction mixture was confirmed. Consequently, the formation of a slight amount of the title compound at a slight amount was confirmed, but great quantities of byproducts were also observed, although no raw materials remained.

Referential Example 6

Synthesis of 2-{[4-(3-methoxypropoxy)-3-methylpyridin-2-yl]methylsulfinyl}-1H-benzimidazole (Rabeprazole free base)
(oxidant:manganese dioxide)

The Compound I (1 g, 2.9 mmol) was dissolved in dichloromethane (10 ml), followed by the addition of active manganese oxide (5 g) at room temperature. After reacting at room temperature for 21 hr, the change of the reaction solution was confirmed by HPLC. Consequently, no formation of the title compound was confirmed.

Referential Example 7

Synthesis of 2-{[4-(3-methoxypropoxy)-3-methylpyridin-2-yl]methylsulfinyl}-1H-benzimidazole (Rabeprazole free base) (oxidant:pyridinium dichromate)

The Compound I (1 g, 2.9 mmol) was dissolved in dichloromethane (10 ml), followed by the addition of pyridinium dichromate (1.1 g, 2.9 mmol) at room temperature. After reacting at room temperature for 21 hr, the change of the reaction mixture was confirmed by HPLC. Consequently, the formation of 3.2% (yield) of the title compound was confirmed but 96% of the Compound I still remained unreactive.

Referential Example 8

Synthesis of 2-{[4-(3-methoxypropoxy)-3-methylpyridin-2-yl]methylsulfinyl}-1H-benzimidazole (Rabeprazole free base) (oxidant:cerium diammonium nitrate)

The Compound I (1 g, 2.9 mmol) was suspended in a solvent mixture of acetonitrile (20 ml) and water (10 ml), and then, cerium diammonium nitrate (1.59 g, 2.9 mmol) was added dropwise thereinto. After reacting at room temperature for 20 hr, the change of the reaction mixture was confirmed by HPLC. Consequently, the formation of 0.5% of the title compound was observed, but 98% of the Compound I still remained unreactive The above results apparently indicate that the objective sulfoxide (II) can be obtained in a good yield and safety by the present invention.

Additionally, the cost of perborate, specifically sodium perborate.tetrahydrate, is about ¹/₁₀-fold the cost of m-chloroperbenzoic acid, so the present invention is extremely excellent in the respect of the production cost.

Further, perborate, specifically sodium perborate.tetrahydrate, N-halosuccinimide, 1,3-dihalo-5,5-dimethylhydantoin and dichloroisocyanurate are not dangerous materials and are also handled easily at a greater amount. Thus, the present invention is proved to be an industrially excellent method for producing sulfoxide (II).

What is claimed is:

1. A method for producing a sulfoxide (II) represented by the following formula (II):

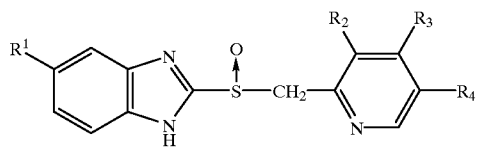

(II)

(wherein $R^1$, $R^2$, $R^3$ and $R^4$ have the same meanings as defined below), which comprises the step of oxidizing a thioether (I) represented by the following formula (I):

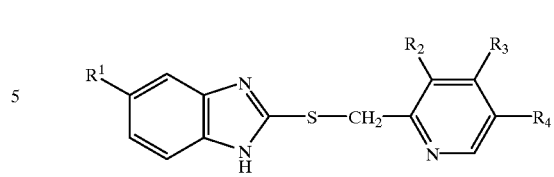

(I)

(wherein $R^1$ represents hydrogen atom, methoxy group or difluoromethoxy group; $R^2$ represents methyl group or methoxy group; $R^3$ represents 3-methoxypropoxy group, methoxy group or 2,2,2-trifluoroethoxy group; and $R^4$ represents hydrogen atom or methyl group) with a) a perborate in the presence of an acid anhydride or a metal catalyst or b) an N-halosuccinimide, a 1,3-dihalo-5,5-dimethylhydantoin or dichloroisocyanurate in the presence of a base.

2. The method as claimed in claim 1, which comprises the step of oxidizing with a) a perborate in the presence of an acid anhydride or a metal catalyst.

3. The method as claimed in claim 2, wherein the perborate is sodium perborate.

4. The method as claimed in claim 2, wherein the perborate is sodium perborate tetrahydrate or sodium perborate monohydrate.

5. The method as claimed in claim 2, wherein the perborate is used in an amount of 0.9 to 1.5 equivalents to the thioether (I).

6. The method as claimed in claim 2, wherein the oxidative reaction is conducted in methanol, ethanol, propanol and mixture solvents such as methanol/toluene, ethanol/toluene, propanol/toluene, water/methanol, water/ethanol, water/propanol and toluene/dimethylformamide or acetic acid.

7. The method as claimed in claim 2, which is conducted in the presence of the acid anhydride.

8. The method as claimed in claim 7, wherein the acid anhydride is at least one selected from the group consisting of acetic anhydride, propionic anhydride, butyric anhydride, succinic anhydride, maleic anhydride, benzoic anhydride and phthalic anhydride.

9. The method as claimed in claim 7, wherein the acid anhydride is used in an amount of 0.9 to 1.5 equivalents to the thioether (I).

10. The method as claimed in claim 7, wherein the acid anhydride is used in an amount of 1.0 to 2.0 equivalents to the perborate, and of 0.9 to 1.5 equivalents to the thioether (I).

11. The method as claimed in claim 2, which is conducted in the presence of the metal catalyst.

12. The method as claimed in claim 11, wherein the metal catalyst is at least one selected from the group consisting of vanadium pentaoxide, vanadyl acetylacetonate, molybdenum oxide actylacetonate, ammonium heptamolybdate tetrahydrate, ammonium molybdate, sodium vanadate, titanium tetraisopropoxide, titanium trichloride, tellurium dioxide, selenium dioxide, methyl trioxorhenium and tungsten oxide.

13. The method as claimed in claim 11, wherein the metal catalyst is used in an amount of 0.05 to 0.15 equivalent to the perborate.

14. The method as claimed in claim 1, which comprises the step of oxidizing with b) N-halosuccinimide, 1,3-dihalo-5,5-dimethylhydantoin or dichloroisocyanurate in the presence of a base.

15. The method as claimed in claim 14, wherein the N-halosuccinimide is N-chlorosuccinimide or N-bromosuccinimide.

16. The method as claimed in claim 14, wherein the N-halosuccinimide is used in an amount of 0.9 to 1.5 equivalents to the thioether (I).

17. The method as claimed in claim 14, wherein the 1,3-dihalo-5,5-dimethylhydantoin is 1,3-dichloro-5,5-dimethylhydantoin or 1,3-dibromo-5,5-dimethylhydantoin.

18. The method as claimed in claim 14, wherein the 1,3-dihalo-5,5-dimethylhydantoin is used in an amount of 0.4 to 0.8 equivalent to the thioether (I).

19. The method as claimed in claim 14, wherein the dichloroisocyanurate is sodium dichloroisocyanurate or potassium dichloroisocyanurate.

20. The method as claimed in claim 19, wherein the dichloroisocyanurate is used in an amount of 0.4 to 0.8 equivalent to the thioether (I).

21. The method as claimed in claim 14, wherein the base is an inorganic base.

22. The method as claimed in claim 21, wherein the base is at least one selected from the group consisting of sodium hydroxide, potassium hydroxide, lithium hydroxide, sodium carbonate, potassium carbonate, sodium hydrogen carbonate, potassium hydrogen carbonate, sodium phosphate, potassium phosphate, sodium hydrogen phosphate, sodium formate, potassium formate, sodium acetate and potassium acetate.

23. The method as claimed in claim 21, wherein the base is used in an amount of 0.9 to 3.0 equivalents to the N-halosuccinimide, and of 0.4 to 1.5 equivalents to the 1,3-dihalo-5,5-dimethylhydantoin or dichloroisocyanurate salt.

24. The method as claimed in claim 14, wherein the oxidation is conducted in the solvent at least one selected from the group consisting of N,N-dimethylformamide, acetonitrile, toluene, tetrahydrofuran, lower fatty acid esters and water.

25. The method as claimed in claim 14, wherein the oxidation is conducted in a solvent at least one selected from the group consisting of N,N-dimethylformamide, acetonitrile, toluene, tetrahydrofuran and lower fatty acid esters, in the presence of water.

26. The method as claimed in claim 1, wherein the amount of perborate is in the range of 0.8 to 1.7 equivalents to thioether (I).

27. The method as claimed in claim 1, wherein the amount of N-halosuccinimide is 0.8 to 1.7 equivalents to thioether (I).

28. The method as claimed in claim 1, wherein the amount of 1,3-dihalo-5,5-dimethylhydantoin is in the range of 0.3 to 1.0 equivalent to thioether (I).

29. The method as claimed in claim 1, wherein the amount of dichloroisocyanurate is in the range of 0.3 to 1.0 equivalent to thioether (I).

30. The method as claimed in claim 1, wherein the amount of acid anhydride is in the range of 0.8 to 1.7 equivalents to thioether (I).

31. The method as claimed in claim 1, wherein the amount of metal catalyst is 0.05 to 0.15 equivalent to perborate.

32. The method as claimed in claim 1, wherein the amount of base is 0.8 to 4.0 equivalents to N-halosuccinimide.

33. The method as claimed in claim 1, wherein the amount of base is 0.4 to 2.0 equivalents to 1,3-dihalo-5,5-dimethylhydrantoin or dichloroisocyanurate.

34. The method as claimed in claim 24, wherein the amount of water is in the range of 0.1 to 50 ml per 1 g of thioether (I).

35. The method as claimed in claim 24, wherein the amount of solvent ranges from 1 to 100 ml per 1 g of thioether (I).

* * * * *